(12) United States Patent
Lam et al.

(10) Patent No.: US 11,166,804 B2
(45) Date of Patent: Nov. 9, 2021

(54) EMBOLIC PROTECTION DEVICE

(71) Applicant: Terumo Corporation, Tokyo (JP)

(72) Inventors: Cang Lam, Tustin, CA (US); Priscilla Tsai, Rancho Santa Margarita, CA (US); Juan Valencia, Santa Ana, CA (US); Jacqueline Macias, South Gate, CA (US); Kaushik Joshi, Tustin, CA (US); Arnold Tuason, Claremont, CA (US)

(73) Assignee: Terumo Corporation, Tokyo (JP)

( * ) Notice: Subject to any disclaimer, the term of this patent is extended or adjusted under 35 U.S.C. 154(b) by 467 days.

(21) Appl. No.: 15/615,550

(22) Filed: Jun. 6, 2017

(65) Prior Publication Data

US 2017/0265983 A1 Sep. 21, 2017

Related U.S. Application Data

(63) Continuation of application No. 14/217,017, filed on Mar. 17, 2014, now Pat. No. 9,693,852.
(Continued)

(51) Int. Cl.
*A61F 2/01* (2006.01)

(52) U.S. Cl.
CPC ...... *A61F 2/0105* (2020.05); *A61F 2002/016* (2013.01); *A61F 2210/0076* (2013.01); *A61F 2230/005* (2013.01); *A61F 2230/0006* (2013.01); *A61F 2230/0008* (2013.01); *A61F 2230/008* (2013.01); *A61F 2230/0067* (2013.01); *A61F 2230/0076* (2013.01); *A61F 2230/0078* (2013.01); *A61F 2250/0017* (2013.01); *A61F 2250/0039* (2013.01); *Y10T 29/49826* (2015.01)

(58) Field of Classification Search
CPC ........ A61F 2/01; A61F 2/0105; A61F 2/0108; A61F 2/011; A61F 2/013; A61F 2/016; A61B 17/22031; A61B 2017/2212
See application file for complete search history.

(56) References Cited

U.S. PATENT DOCUMENTS 5,910,154 A 6/1999 Tsugita et al.
6,142,987 A 11/2000 Tsugita
(Continued)

FOREIGN PATENT DOCUMENTS

WO WO1997/048326 A2 12/1997

OTHER PUBLICATIONS

WIPO, International Preliminary Examining Authority (U.S. Patent and Trademark Office), International Preliminary Report on Patentability dated Oct. 1, 2015 in International Patent Application No. PCT/US2014/030738, 9 pages.
(Continued)

*Primary Examiner* — Sarah W Aleman
(74) *Attorney, Agent, or Firm* — Inskeep IP Group, Inc.

(57) ABSTRACT

An embolic protection device includes an expandable and contractible filter that can be supported by one or more struts. The struts can be connected to the filter or interwoven into the filter, so as to assist in the expansion and contraction of the filter. In one embodiment, the proximal ends of the struts connect to a joint that is fixed in position relative to a delivery wire, while the distal end of the filter connect to a joint that slides relative to the delivery wire.

14 Claims, 17 Drawing Sheets

Related U.S. Application Data

(60) Provisional application No. 61/799,114, filed on Mar. 15, 2013.

(56) References Cited

U.S. PATENT DOCUMENTS

| | | | |
|---|---|---|---|
| 6,186,978 B1 | 2/2001 | Samson et al. | |
| 6,364,895 B1 * | 4/2002 | Greenhalgh | A61F 2/013 |
| | | | 606/200 |
| 6,485,500 B1 | 11/2002 | Kokish et al. | |
| 6,511,496 B1 | 1/2003 | Huter et al. | |
| 6,569,183 B1 | 5/2003 | Kim et al. | |
| 6,629,952 B1 | 10/2003 | Chien et al. | |
| 6,702,834 B1 | 3/2004 | Boylan et al. | |
| 6,716,231 B1 * | 4/2004 | Rafiee | A61F 2/01 |
| | | | 606/200 |
| 6,746,469 B2 | 6/2004 | Mouw | |
| 6,866,677 B2 | 3/2005 | Douk et al. | |
| 7,780,694 B2 | 8/2010 | Palmer et al. | |
| 7,850,708 B2 | 12/2010 | Pal | |
| 8,182,507 B2 * | 5/2012 | Anderson | A61B 17/221 |
| | | | 606/200 |
| 8,361,105 B2 | 1/2013 | Adams et al. | |
| 8,377,092 B2 * | 2/2013 | Magnuson | A61F 2/013 |
| | | | 606/200 |
| 8,632,562 B2 * | 1/2014 | Pal | A61F 2/013 |
| | | | 606/200 |
| 2001/0020175 A1 | 9/2001 | Yassour et al. | |
| 2002/0128680 A1 * | 9/2002 | Pavlovic | A61F 2/01 |
| | | | 606/200 |
| 2002/0169474 A1 | 11/2002 | Kusleika et al. | |
| 2003/0100917 A1 | 5/2003 | Boyle et al. | |
| 2003/0176886 A1 | 9/2003 | Wholey et al. | |
| 2004/0093012 A1 * | 5/2004 | Cully | B23P 11/00 |
| | | | 606/200 |
| 2005/0038468 A1 | 2/2005 | Panetta et al. | |
| 2006/0224180 A1 | 10/2006 | Anderson et al. | |
| 2006/0287701 A1 | 12/2006 | Pal | |
| 2007/0219579 A1 * | 9/2007 | Paul, Jr. | A61F 2/013 |
| | | | 606/200 |
| 2010/0152829 A1 | 6/2010 | Edelman et al. | |
| 2010/0191273 A1 | 7/2010 | Keating | |

OTHER PUBLICATIONS

WIPO, U.S. International Search Authority, International Search Report and Written Opinion dated Nov. 14, 2014 in International Patent Application No. PCT/US2014/030738, 12 pages.

European Patent Office, Supplementary European Search Report dated Nov. 8, 2013 in European Patent Application No. 12749846.7—1506/2667925, 11 pages.

* cited by examiner

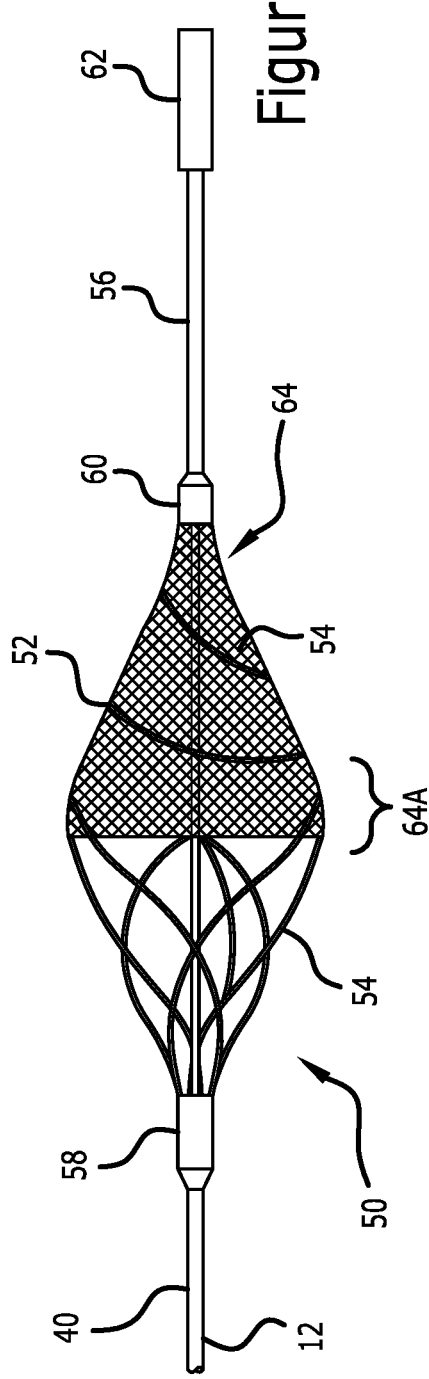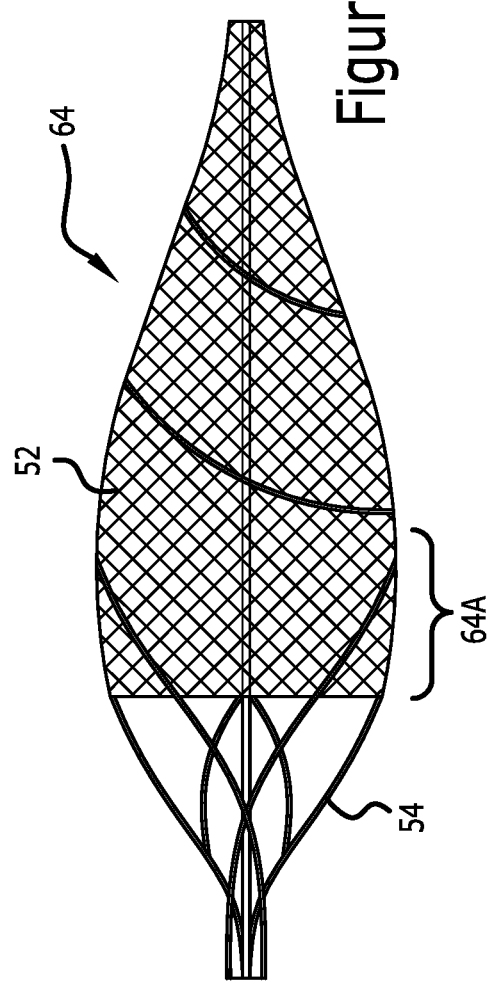

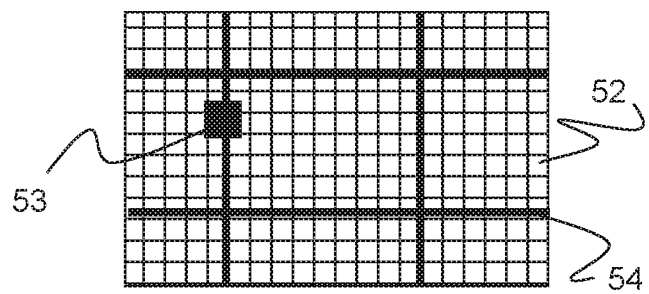
Figure 27
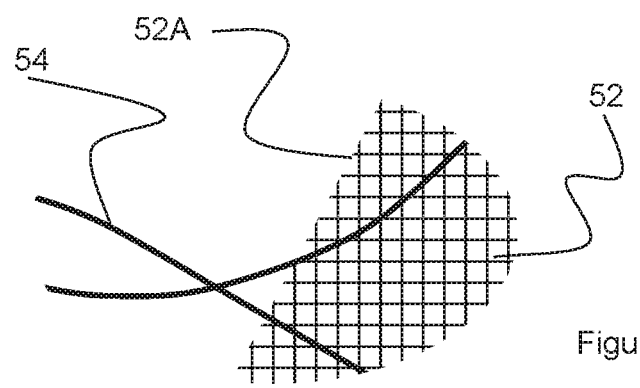
Figure 28
Figure 29
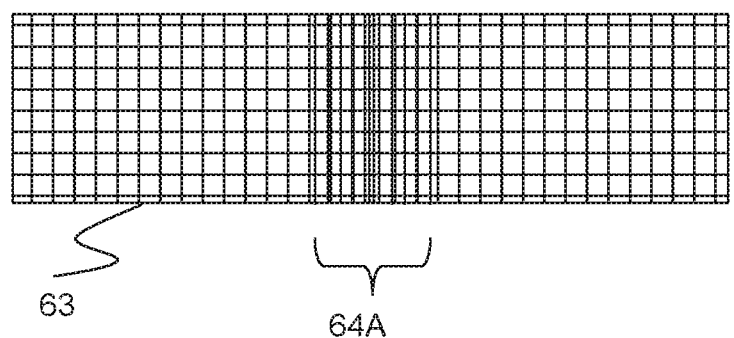

EMBOLIC PROTECTION DEVICE

RELATED APPLICATIONS

This application is a continuation of and claims priority to U.S. patent application Ser. No. 14/217,017 filed Mar. 17, 2014 entitled Embolic Protection Device, which claims benefit of and priority to U.S. Provisional Application Ser. No. 61/799,114 filed Mar. 15, 2013 entitled Embolic Protection Device, both of which are hereby incorporated herein by reference in their entireties.

BACKGROUND OF THE INVENTION

During certain surgical procedure, such as catheter-based treatments, a physician's surgical tools can sometimes dislodge embolic particles. These embolic particles typically include thrombus, atheroma, and lipids, which, once dislodged, can cause blockages in downstream vessels. Hence, these embolic particles can result in serious surgical complications, such as stroke or even death.

One method for reducing the risk of these complications is to deploy an embolic filter downstream of a surgical treatment site, thereby catching any particles that may become dislodged. Once caught, the filter must be carefully closed and withdrawn from the patient, such that the captured particles do not spill out.

SUMMARY OF THE INVENTION

One embodiment is directed to an embolic protection device comprising a filter, one or more struts connected to said filter, a delivery wire, a sliding joint, one or more fixed joints, and a flexible member between said sliding joint and a fixed joint.

In one embodiment the embolic protection device includes a flexible member which sits distal relative to the filter.

In another embodiment the embolic protection device includes a flexible member which spans the length between the filter and the struts.

In another embodiment the embolic protection device includes a flexible member which spans a portion of the length between the filter and the struts.

In one embodiment the embolic protection device includes a sliding joint and/or fixed joint that has a shape adapted to mate with a delivery device used to deliver the embolic protection device.

In one embodiment an embolic protection device includes a filter wherein said filter is inverted.

In another embodiment an embolic protection device includes a filter wherein said filter is everted.

In another embodiment, an embolic protection device includes a rapid exchange delivery catheter.

In another embodiment, an embolic protection device includes a fixed joint that can rotate relative to a delivery wire.

In another embodiment, an embolic protection device includes a filter formed from a plurality of large wire and a plurality of small wires. The large wires can additionally form the struts on the device's proximal end. Additionally, a proximal fixed joint and a distal sliding joint are disposed on a tube, through which a delivery wire is disposed.

In another embodiment, an embolic protection device includes a filter having a heat-set open-end portion having a relatively less porous or more compressed configuration than the more distal portions.

In another embodiment, an embolic protection device includes a filter having a heat-set open-end portion having a relatively less porous or more compressed configuration than the more distal portions. As the filter reduces in diameter, the more-compressed region more quickly reduces in diameter, partially closing around the mouth of the filter.

In another embodiment, an embolic protection device includes a filter having distal struts or loop shapes that assist in opening and closing the filter.

In another embodiment, an embolic protection device is configured to operate as a rapid exchange or monorail device, accommodating both the delivery wire and the guidewire.

BRIEF DESCRIPTION OF THE DRAWINGS

These and other aspects, features and advantages of the invention will be apparent and elucidated from the following description of embodiments of the present invention, reference being made to the accompanying drawings, in which:

FIGS. 25-26 illustrate an embolic protection device in an expanded state.

FIGS. 27-28 illustrate magnified views of the filter of the device from FIG. 25.

FIGS. 29-31 illustrate various views for creating the device of FIG. 25.

FIGS. 44-45 illustrates a catheter-cutting device for opening a distal end of a delivery device.

DESCRIPTION OF EMBODIMENTS

Figure 1:
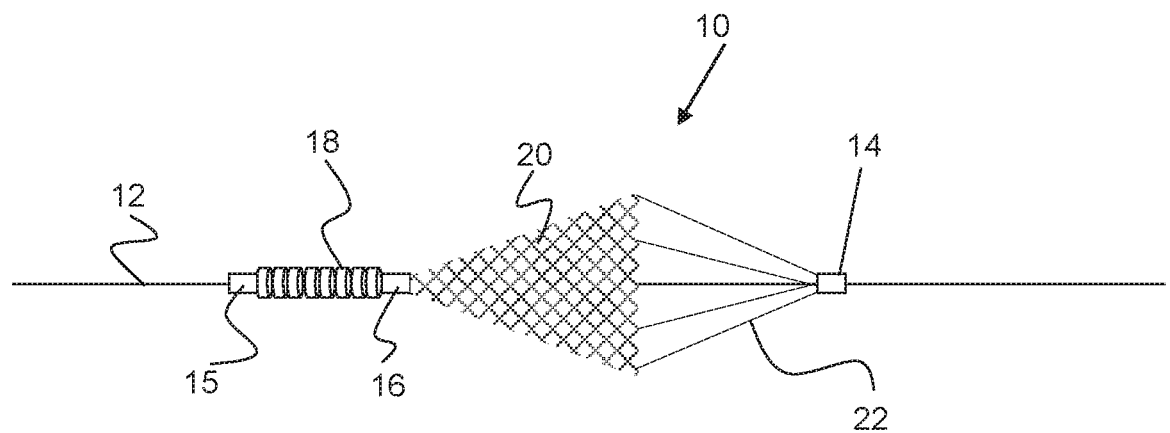
FIGS. 1-3 illustrate an embolic protection device in an expanded state.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The terms thrombus, emboli, embolic particles, and similar terms are used throughout this specification. Unless specifically noted otherwise, these terms are used interchangeably and generally refer to any unwanted, undesirable, or otherwise dangerous particle that could be located or caused to locate within a vessel of a human body.

The present specification and drawings contain several different embodiments that each contain different elements and configurations. While these specific embodiments have been described, it should be understood that any of the elements and/or configurations can be combined with any of the other embodiments presented.

Embolic protection devices may be used to trap thrombus dislodged during a thrombus removing procedure. In one example, an embolic protection device is placed distal of the target area. A balloon and/or stent are used to expand the clogged vessel, and the embolic protection device catches any dislodged thrombus to prevent it from migrating downstream.

Figure 2:
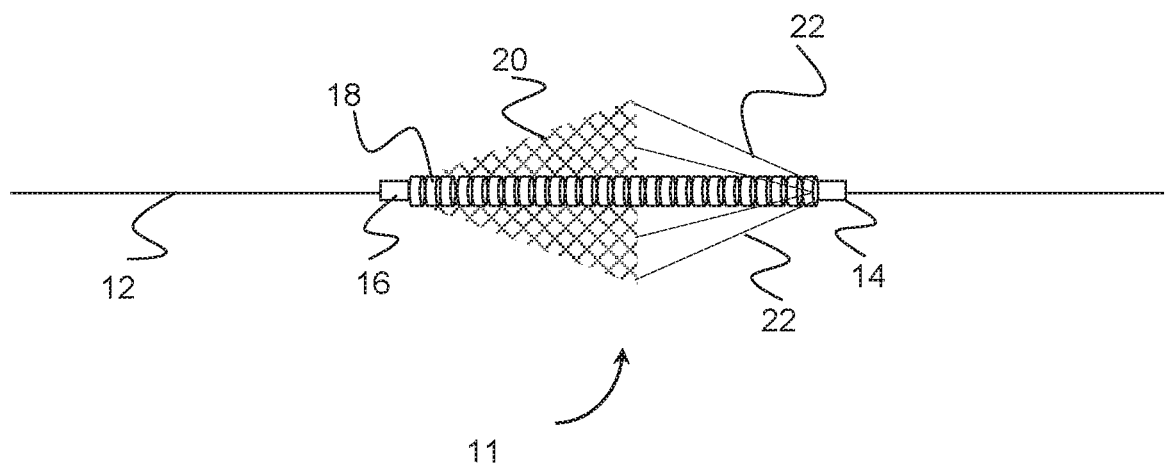
Figure 3:
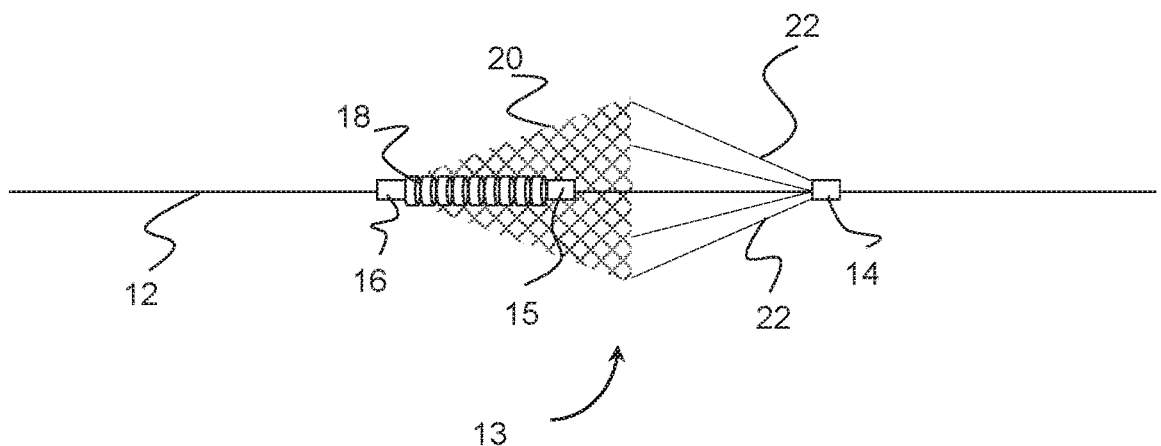
Figure 4:
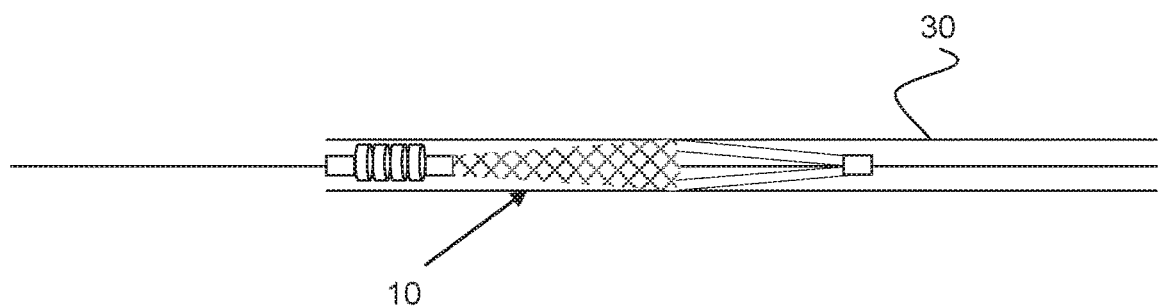
FIGS. 4-6 illustrates an embolic protection device in a compressed state (i.e. during delivery).
Figure 5:
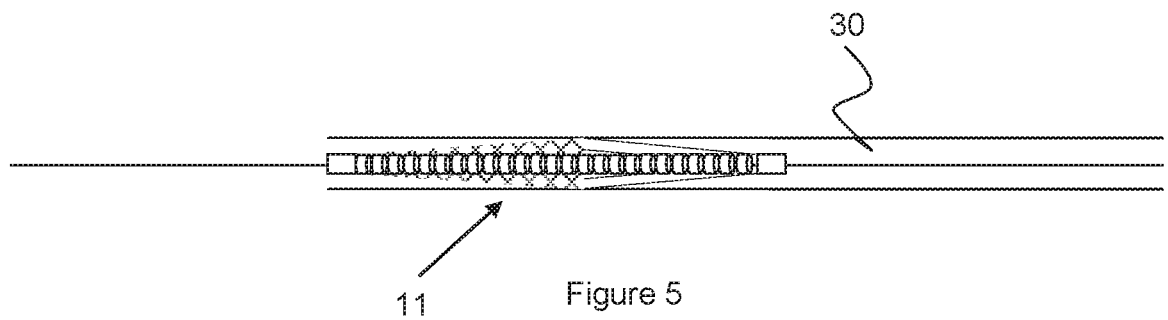
Figure 6:
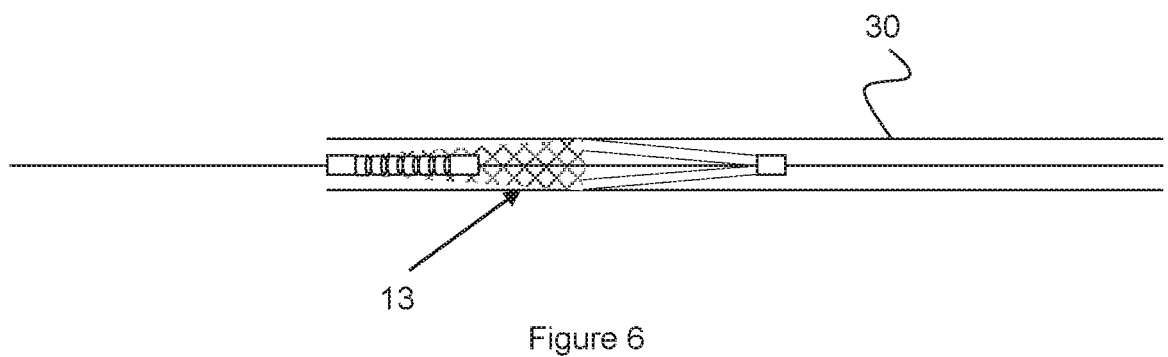

FIGS. 1-3 show various embodiments for the embolic protection device that each have an expanded configuration for trapping embolic particles and a contracted configuration which it adopts when being delivered through a delivery device 30 (i.e., microcatheter) as shown in FIG. 4-6. In each of these embodiments, the embolic protection devices 10, 11, and 13 sit over a delivery wire 12 and include a filter 20 used to capture thrombus. Preferably, the filter 20 is a braid or mesh formed from one or more wires (e.g., wires composed of Nitinol, stainless steel, cobalt chromium, and/or a polymer material). Radiopaque material (i.e. tantalum or platinum) could also be used in the constituent wires comprising the mesh. This mesh or braided filter 20 can be formed from a single mesh/braid layer or from multiple layers (e.g., a larger porosity layer and a smaller porosity layer). In another embodiment, the filter is formed from a single solid material (e.g., a laser-cut tube).

Each of the devices 10, 11, and 13 include one or more struts 22 connected to various locations on the filter 20, to assist in expanding and contracting the filter 20 during a procedure. Since the struts 22 are oriented proximally or closest to the delivery device 30, they act to close the filter 20 as each of the devices 10, 11, and 13 are retracted within the delivery device 30.

The struts 22 and filter 20 are each able to expand over the deliver wire 12 via a fixed joint 14 and a sliding joint 16. The struts 22 are connected to the fixed joint 14, which is stationary relative to the delivery wire 12. The sliding joint 16 is connected to a distal end of the filter 20, allowing it to slide relative to the deliver wire 12 as the device expands and contracts.

The filter 20 forms a generally conical shape that functions to capture thrombus emanating from a more proximal portion of the vessel. Therefore the open (enlarged) portion of filter 20 is proximal relative to the portion of the filter connected to the sliding joint 16, and struts 22 are proximal relative to filter 20.

The devices 10, 11, and 13 can also include a compression member 18 that can assist or bias the device into an expanded position. Referring to the device 10 shown in FIG. 1, the compression member 18 is disposed over the delivery wire 12 and is connected to sliding joint 16 and a fixed joint 15, all located distally of the filter 20. The compression member 18 can include a metal or plastic spring-like member, a solid resilient polymer member, an elastic material, or materials with a similar behavior/functionality.

FIG. 4 shows the compressed configuration of the embolic protection device 10 when positioned in a delivery device 30 (i.e. a microcatheter). When the filter 20 is collapsed during placement within a delivery device 30, the filter 20 and struts 22 exert a force on sliding joint 16. Sliding joint 16 moves distally toward the fixed joint 15 resulting in compression of the compression member 18. When the embolic protection device 10 is released from the delivery device 30, the compression member 18 moves from a compressed to expanded configuration, proximally pushing the filter 20 and struts 22 to an open or expanded configuration. Since the filter 20 and/or struts 22 may be composed of shape-memory materials that are biased or "heat-set" to an expanded configuration, these components may further exert expansile force after deployment from the delivery device 30. Further, the fixed joint 15 anchors the compression member 18, which in turn helps to create a backstop for over-expansion of the filter 20.

Referring to the device 11 of FIG. 2, the compression member 18 spans the region between sliding joint 16 and the fixed joint 14. FIG. 5 shows the compressed configuration of the embolic protection device 11 of FIG. 2 when positioned in a delivery device 30 (i.e. a microcatheter). When filter 20 is collapsed during placement within a delivery device 11, the filter 20 and compression member 18 exert force on sliding joint 16, causing the sliding joint 16 to slide in a distal direction, stretching out the compression member. When the device 11 is removed from the delivery device 30, compression member 18 will exert an unrestrained pulling force between joints 14 and 16, causing the filter 20 to expand, and maintain its expanded shape. Again, since the filter 20 and/or struts 22 may be composed of shape-memory materials that are biased or "heat-set" to an expanded configuration, these components may further exert expansile force after deployment from the delivery device 30.

Referring to the device 13 in FIG. 3, the compression member 18 is coupled between sliding joint 16 and distal fixed joint 15 (distal fixed joint 15 is distal relative to fixed joint 14). In contrast to the device 10 embodiment shown in FIG. 1, the compression member 18 is located within the filter 20. In contrast to the device 11 embodiment shown in FIG. 2, the compression member 18 only expands partially between the sliding joint 16 and fixed joint 14.

FIG. 6 shows the compressed configuration of the embolic protection device 13 of FIG. 3. As the device 13 exits the delivery device 30, the compression member 18 contracts, pulling the sliding joint 16 proximally towards the fixed joint 15. Again, since the filter 20 and/or struts 22 may be composed of shape-memory materials that are biased or "heat-set" to an expanded configuration, these components may further exert expansile force after deployment from the delivery device 30.

Figure 7:
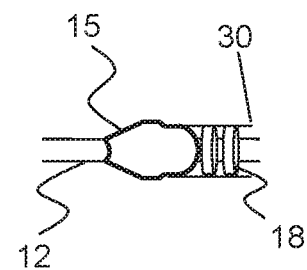
FIG. 7 illustrates a fixed joint used in an embolic protection device.

FIG. 7 shows an embodiment of the configuration of distal fixed joint 15 from FIG. 1. In this embodiment the distal fixed joint 15 has a tapered shape between delivery wire 12 and compression member 18. The fixed joint 15 preferably has a smooth profile and no sharp edges to help reduce blood vessel trauma as the embolic protection device 10 is tracked through the vasculature. The profile of the device is such that it operatively mates with the distal end of delivery device 30. In FIG. 7, the distal fixed joint 15 sits just distal to delivery device 30 and mates with the distal opening of said delivery device 30.

The shape described for the distal fixed joint in FIG. 7 can be used on sliding joint 16 of device 11 and 13 in FIGS. 2 and 3, respectively. In this way, the distal-most joint would effectively function as a 'seal' for the rest of the device as its sits in the delivery device 30.

Figure 8:
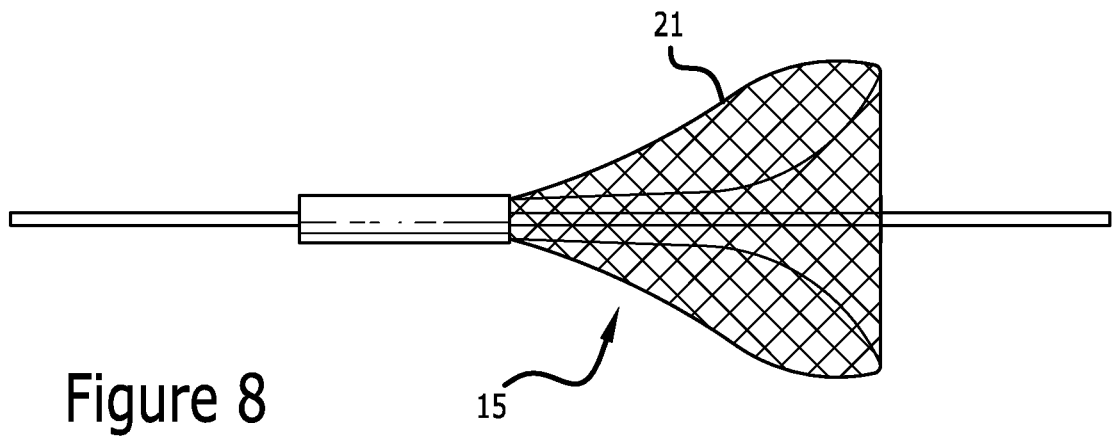
FIG. 8-9 illustrate filters used in an embolic protection device.

In one embodiment shown in FIG. 8, the device 15 includes a filter 21 that is inverted from outside-in, creating a flared outer layer and a reduced inner layer. The filter 21 is pulled inward from a single layer to create the second, underlying layer. In one embodiment, a smaller diameter tube is placed internally within the mesh or braid which forms the filter 20. A portion of the mesh or braid is then pulled through this smaller diameter tube in order to create the smaller diameter region of the filter. The filter 20 can be heat seat into this final shape, the free ends of the filter may be inserted into a common element (i.e. sliding joint 16), or both techniques can be used. Alternatively, the filter 21 is created by placing a larger diameter tube over the external diameter of the mesh or braid, and then pulling it loosely over said tube to create the larger flared region.

Figure 9:
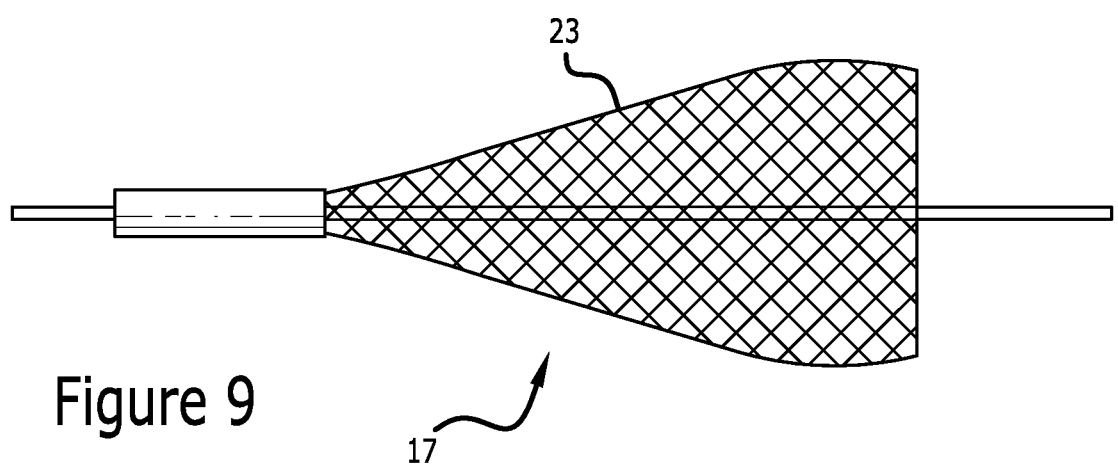
Figure 10:
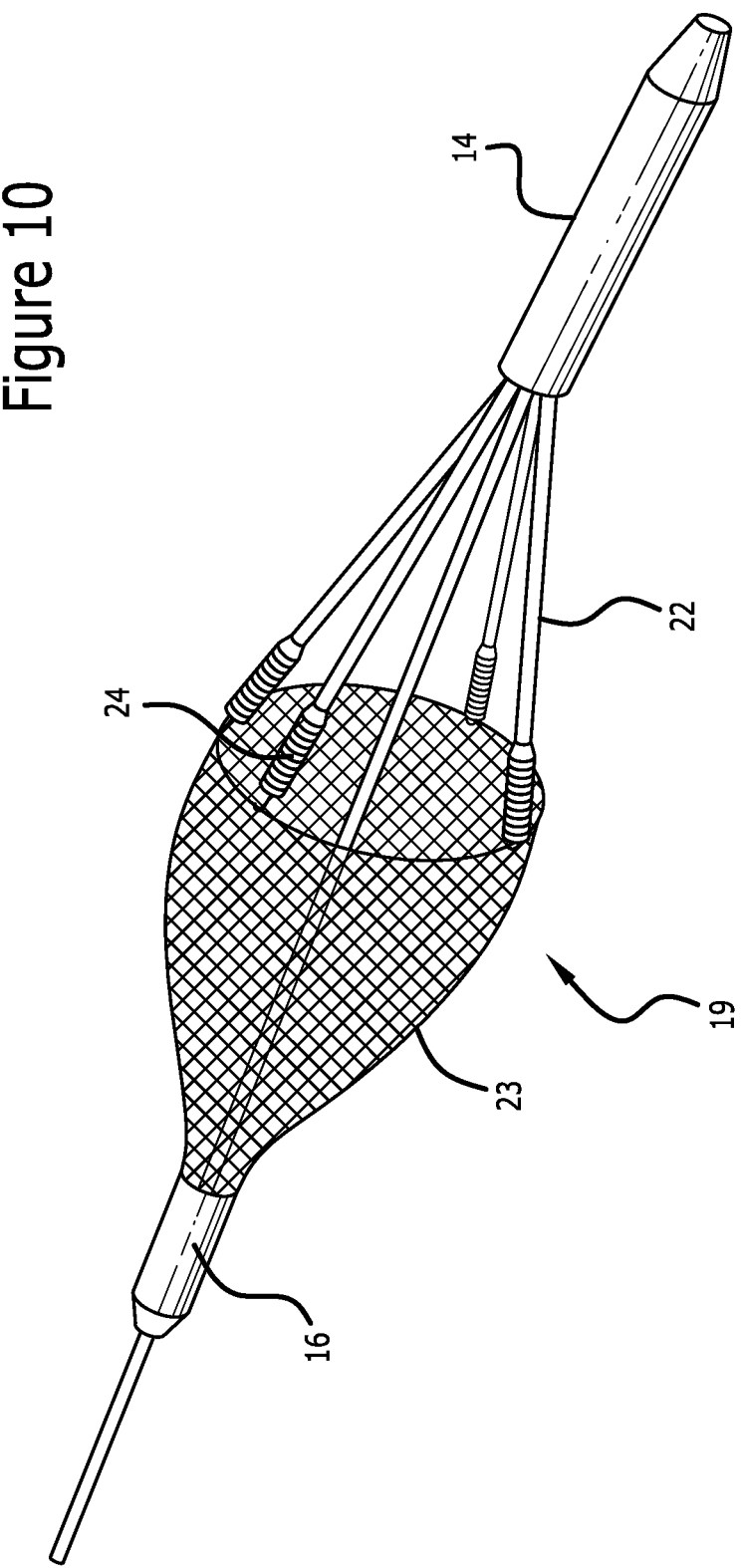
FIGS. 10-11 illustrate a filter and struts used in an embolic protection device.

In another embodiment shown in FIG. 9, the filter 23 of device 17 is inverted from inside-out, forming an inner layer and outer layer. The filter 23 is pulled and folded outward, over itself to produce the outer, second layer. The outer layer can be pulled taut to achieve the lengthier profile shown in FIG. 9 or left loose to achieve a profile similar to the one shown in FIG. 8. In one embodiment, a larger diameter tube is placed external to the mesh or braid which forms the filter. A portion of the mesh or braid is moved over and around the external diameter of the tube to create the second, overlapping region. The filter can be heat seat into this final shape, the free ends of the filter may be inserted into a common element (i.e. sliding joint 16), or both techniques can be used. Alternatively, the filter 23 could be created by placing a smaller diameter tube under the mesh or braid, and then pulling the mesh or braid tautly under said tube to create the underlying region.

As previously described, several embodiments described in this specification include a number of struts 22 that are connected to and support the filter 20. The struts 22 can help control the expansion of filter 20 by providing a controlled restraining force. Since the struts 22, in some embodiments, are connected to fixed joint 14, they help the filter 20 collapse when re-inserting the filter 20 into the delivery device 30. During reinsertion, the struts 22 will provide a restraining force on the filter 20, in combination with the action of the sliding joint 16 and compression member 18. Thus the struts 22 help control the filter 20 expansion, and aid in filter 20 collapse during insertion into the delivery device 30.

The struts 22 can, be constructed in a number of configurations. In one example, metallic struts 22 can be used with the dual layer filter 23 shown in FIG. 9. In one example, the struts 22 connect to both layers of the inverted or everted mesh to provide a stronger anchor point for the connection. The struts 22 may include a connecting member 24 (e.g., a hook shape or loop) to connect to the filter 23. The connecting member 24 may be heat set to form a shape that connects to the filter 23 or may be directly treated to bond to the filter 23. In one example, the connecting member 24 is a coil that encompasses the end of the strut 22 and forms a loop through a pore of the filter 23. This coil helps secure the strut 22 against the filter 23 and provides a surface which is both softer and has a higher surface area to push against the filter. A number of materials can be used for the struts 22, including Nitinol, stainless steel, polymer, radiopaque materials (i.e. tantalum, platinum, or palladium) and combinations therein.

Figure 11:
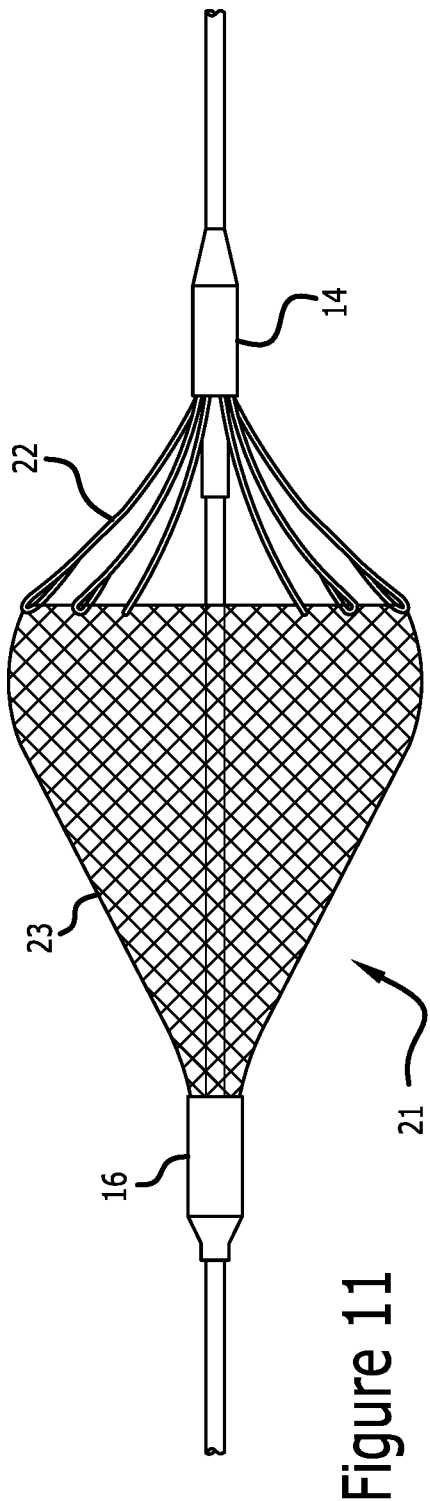

In another example embodiment shown in FIG. 11, the struts 22 are each single wires which extend through pores on the filter 23 and connect back to themselves, forming an end loop. The end of the wires can be fixed to themselves via a connecting component such as a crimped sleeve or can be bonded to each other with an adhesive, welding, similar technique.

Figure 12:
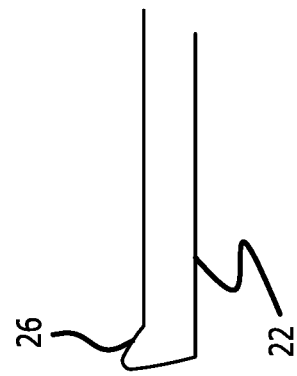

In another example shown in FIG. 12, the one or more struts 22 have a curved region 26 adapted to mate with a corresponding curved region of the filter 20. This curved region 26 can extend from a single strut 22 or between two struts 22 and can further be welded or heat treated to fix to the corresponding curved region of filter 20. This design allows the force created by retracting into the delivery device 30 to spread over a larger area of the filter 20.

Figure 13:
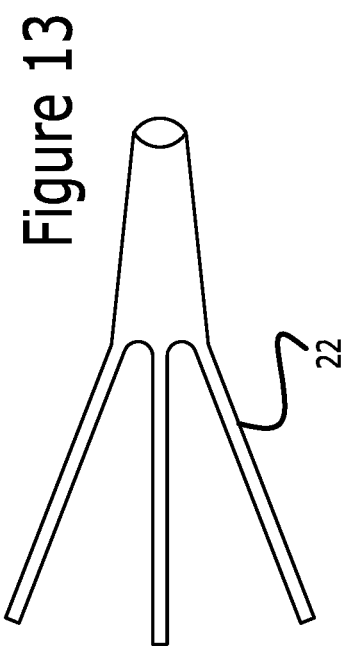
FIGS. 12-13 illustrate struts used in an embolic protection device.

In another example shown in FIG. 13, the struts 22 are constructed from a tube (e.g., a laser-cut Nitinol tube) with a tubular end on one end, and a plurality of fingers on the other end. These fingers act as the strut 22 and are connected to the edges of the filter 22. In this example, the tubular region opposite the fingers may be crimped or fixed to the delivery wire 12, thereby acting as a fixed joint.

Figure 14:
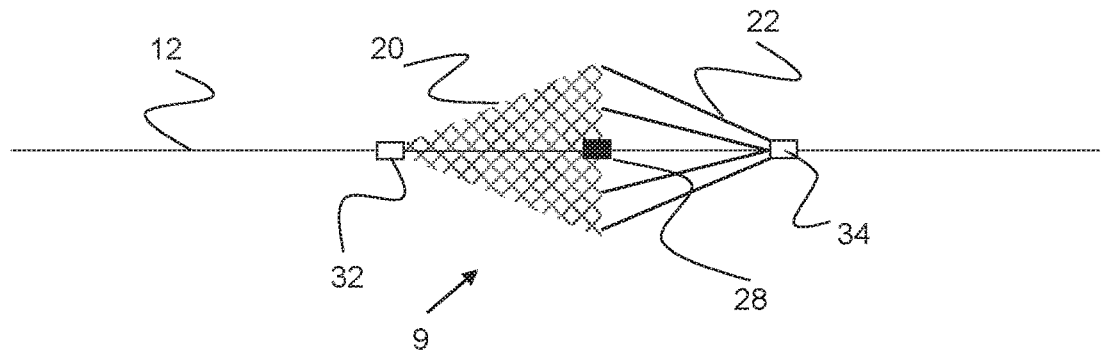
FIGS. 14-16 illustrate a sliding embolic protection device.
Figure 15:
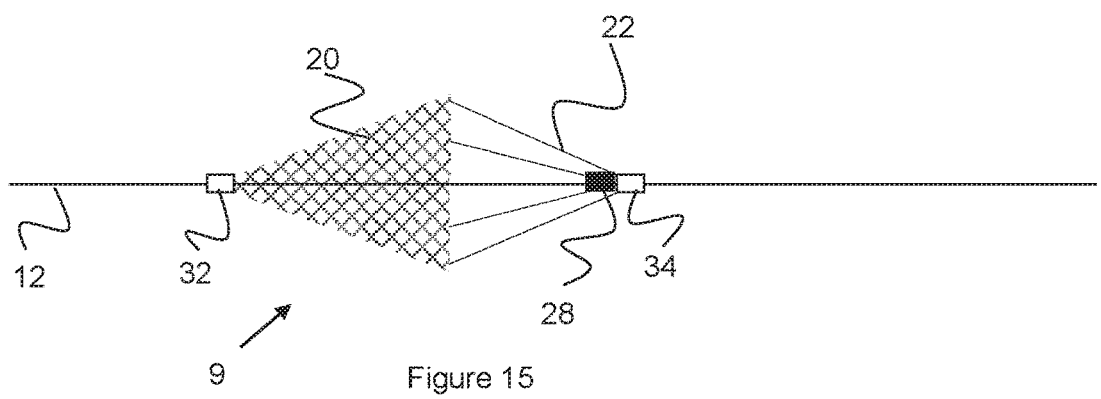
Figure 16:
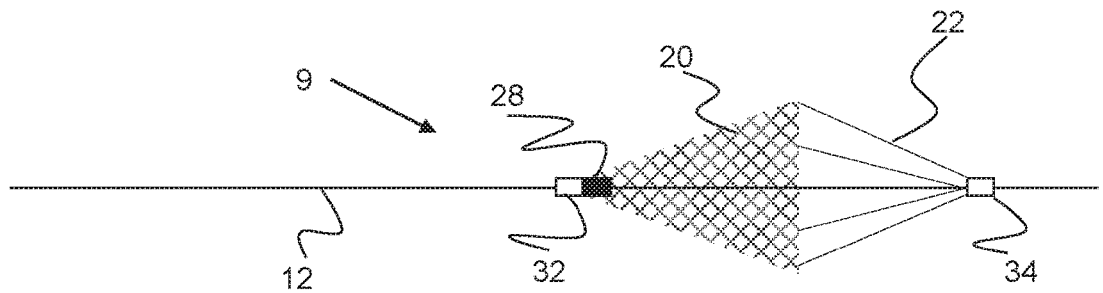

FIG. 14 shows another embodiment of an embolic protection device 9 that includes a sliding joint 34 at the proximal end of the device 9 and a second sliding joint 32 at the distal end of the device 9. A stop 28 is located between the two stops 32 and 34 which limits the proximal and distal translation of the device 9. In other words, the device's distal translation is limited by stop 28 interacting with proximal slider 34 (seen in FIG. 15), and the device's proximal translation is limited by stop 28 interacting with distal slider 32 (seen in FIG. 16). The sliding joints 32, 34 are disposed or captured around the delivery wire 12 but cause minimal friction with the wire, thus allowing the joints 32, 34 to easily slide.

Figure 17:
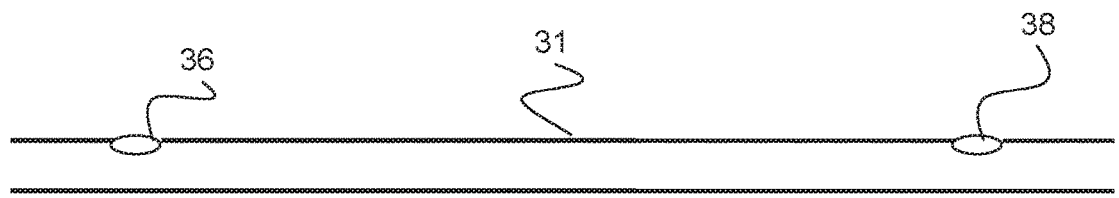
FIGS. 17-18 illustrate a catheter used with an embolic protection device.
Figure 18:
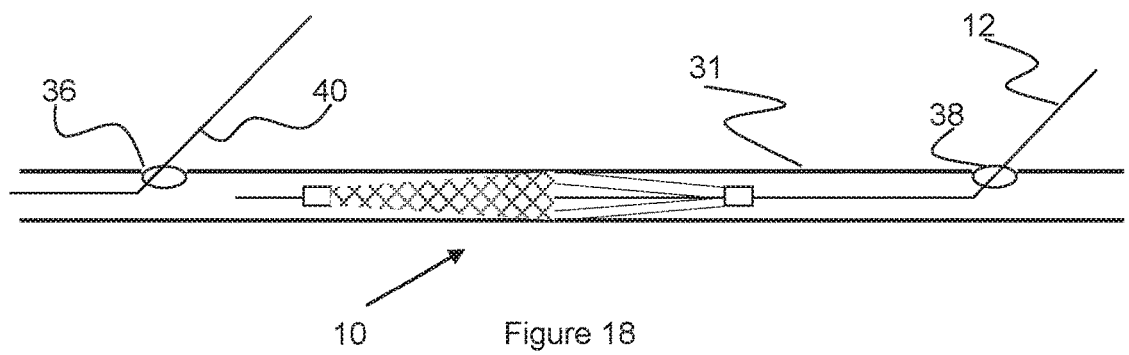
Figure 19:
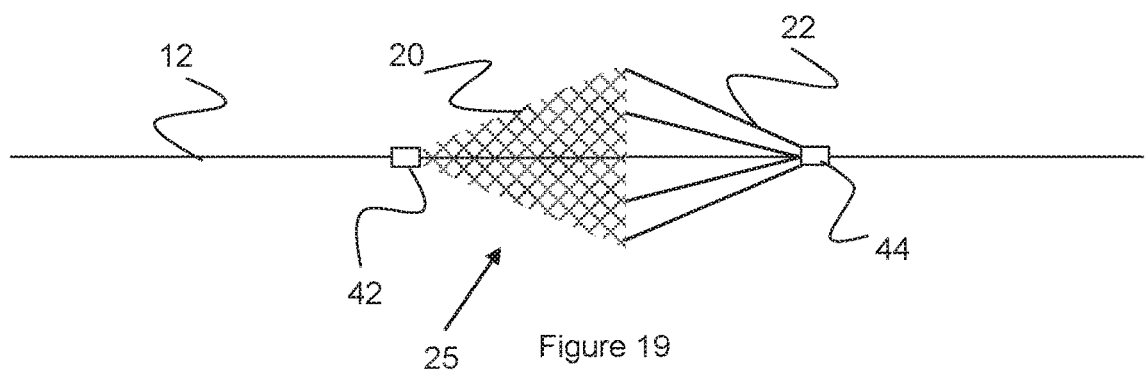
FIG. 19 illustrates an embolic protection device which is rotatable.

FIGS. 17-18 show an embodiment of a rapid exchange catheter 31 used for delivery of an embolic protection device 10 (or any of the devices described in this specification). Catheter 31 includes a distal port 36 used as an access port for a guidewire 40, which, when inserted, is used to track or direct delivery of catheter 31 to a certain target region within the vasculature. Proximal port 38 is used as an access port for the embolic protection device 10, allowing the device 10 to reach the desired target location achieved by the guidewire 40.

In one example the diameter of guidewire 40 and delivery wire 12 can both be about 0.014". Various diameters could also be used, lesser or greater, and this value is only offered as an example.

Another aspect of the present invention can allow one or more of the proximal joints 44 and/or distal joints 42 to be rotatable, as seen in FIGS. 20-24. Preferably, the distal joint 42 is rotatable to allow rotation of the filter 20 in the vasculature as it expands and retracts. This allows the device 10 to better conform to the patient's vessel and reduce any unwanted stress that results in undesirable functionality of the device 10.

Figure 20:
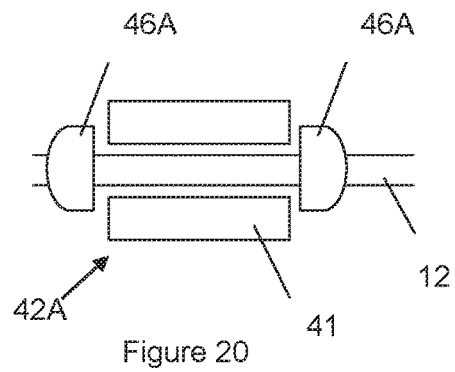
FIGS. 20-24 illustrate several different rotatable joints.

FIG. 20 illustrates one embodiment of a rotatable joint 42A, having two enlarged sections 46A that are fixed from translation and rotation to the delivery wire 12. The outer rotational member 42A may fit directly over the wire 12, thereby capturing the wire 12, while the enlarged sections 46A prevent translational movement of the region 42A.

Hence, the outer rotational member 42A (and anything attached to it) can rotate in place.

Figure 21:
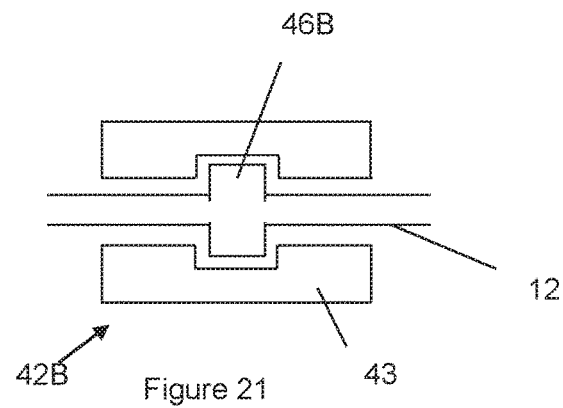

FIG. 21 illustrates another embodiment of a joint 42B in which the outer rotational member 43 includes a recessed cavity that accommodates a fixed, enlarged member 46B. As with the previous joint 42A, the fixed, enlarged member 46B is fixed to the wire 12 to prevent translational or rotational movement. The member 46B is also sized large enough such that it is unable to pass through the reduced diameter portions of the outer rotational member 43. Thus, the outer rotational member 43 effectively captures the member 46B, but can rotate in place.

Figure 22:
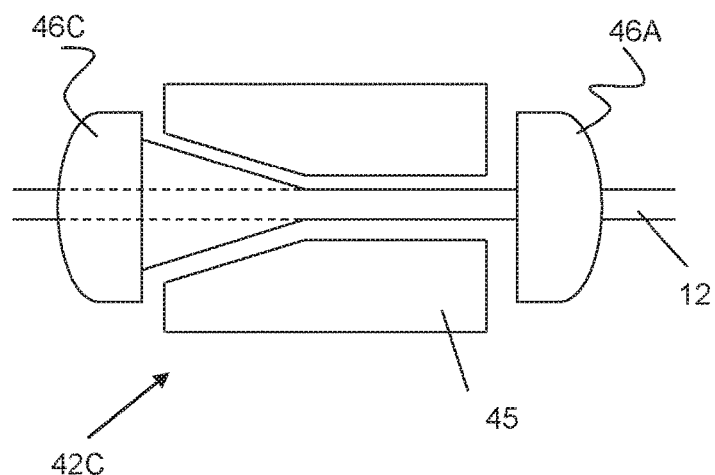
Figure 23:
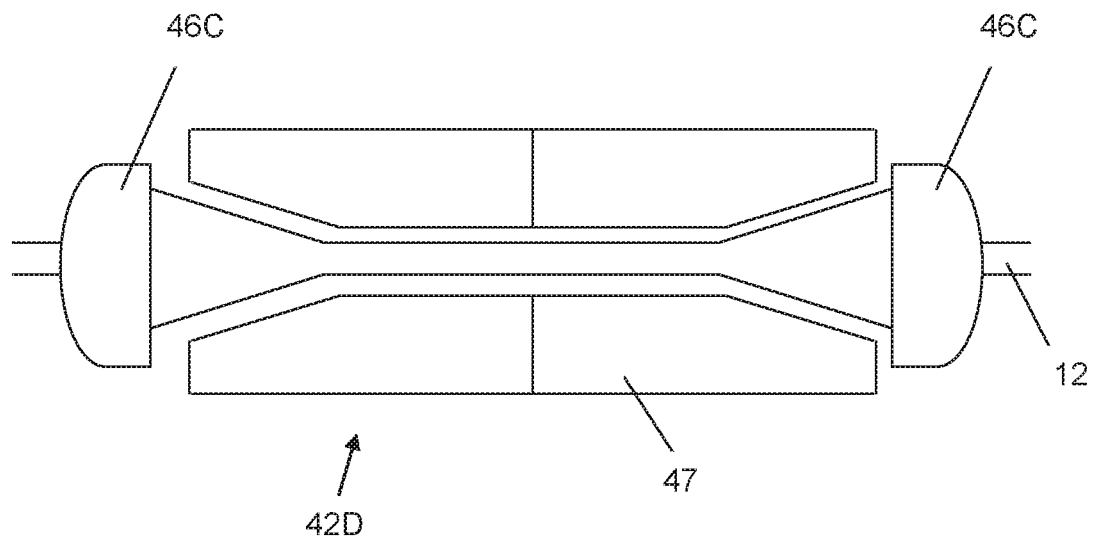
Figure 24:
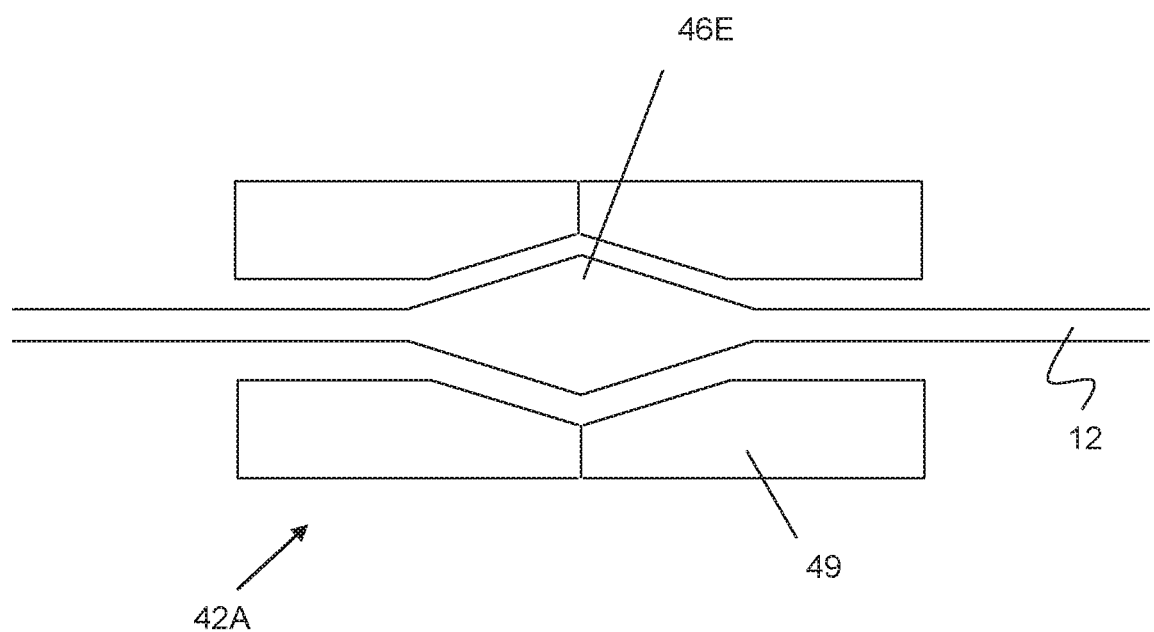

FIG. 22 illustrates another embodiment of a joint 42C that is generally similar to joint 42A, however, one of the fixed, enlarged members 46B includes a tapered region while the outer rotational member 45 includes a reciprocal tapered region. Similarly, FIG. 23 illustrates another embodiment of a joint 42E in which both ends of the outer rotational member 47 have tapered regions that reciprocate with two fixed, enlarged members 46C. Finally, FIG. 24 illustrates yet another embodiment of a joint 42E that is generally similar to joint 42B, but that the outer rotational member 49 includes a tapered, recessed area that captures a reciprocally tapered fixed, enlarged member 46E.

The joints described may be comprised of a variety of materials including Nitinol, stainless steel, cobalt chromium, polymer, radiopaque material (i.e. platinum or tantalum) or various combinations therein. As previously discussed, these rotational joints can be used in any of the embodiments discussed in this specification. Additionally the enlarged members 46A-46E may be offset (or shrunk in respect to the cavity housing) to allow for some translational freedom, in addition to rotation.

FIG. 25 illustrates another embodiment of an embolic protection device 50 that is generally similar to previously described embodiments, in that the device 50 includes an expandable, conical filter 64 having a proximal fixed joint 58 and a distal sliding joint 60. Unlike the previous embodiments, the filter 64 is disposed over a tube 56 (e.g., a polyimide tube) onto which both joints 58 and 60 are located and which allows passage for both the delivery wire 12 and guidewire 40. In this respect, the device 50 functions as a "monorail" or rapid exchange type filter. In one example delivery wire 12 sits within all or a portion of tube 56 (where tube 56 is placed over said delivery wire), in another example delivery wire 12 ends at the proximal end of tube 56.

As seen best in FIGS. 25-27, the filter 64 is preferably composed of a plurality of smaller diameter wires 52 woven with a plurality of larger diameter wires 54. For example, the smaller diameter wires 52 may have a diameter in the range of about 0.0005-0.00225 inch while the larger diameter wires 54 may have a diameter in the range of about 0.00225-0.008 inch. Additionally, about 4 to 16 larger wires 54 can be used and about 72 to 288 smaller diameter wires 52 can be used. As discussed in further detail below, the larger diameter wires 54 can also form the struts on the proximal end of the device 50. In an alternate embodiment, the larger diameter wires 54 may have the same or similar diameter as wires 52, but may be composed of a stronger or stiffer material (e.g., cobalt chromium wires 54 and Nitinol wires 52).

As seen best in FIGS. 25 and 26, when in an expanded configuration, the filter 64 has a generally conical shape with a less porous end portion 64A (i.e., the region near the open end). After the device 50 has captured particles during a procedure and the user begins retracting the filter 64, this end portion 64A expands and reduces in diameter, following the general shape of the proximal larger wires 54. At least partial expansion of this end portion 64A can be seen in FIG. 26. In this respect, the filter 64 cinches or closes around the proximal portion of any particles caught within the filter 64 prior to any substantial reduction in diameter of the remaining, distal portions of the filter 64. In other words, the proximal end of the filter 64 at least partially closes first, preventing the distal end of the filter 64 from squeezing out any of the particles into the patient's vessels. The end portion 64A can be created by heat setting this area to a more compressed configuration than the remaining portions, or can be formed from a varying or different weave pattern. Alternatively, end portion 64A may have a substantially constant diametric profile rather than the reduced profile shown.

FIGS. 28-31 illustrate various example steps that can be used to create the device 50. Referring first to FIG. 29, a tubular stent-like structure 63 can be first woven or braided with the previously discussed wires 52 and 54. The center region 64A (also referred to as end portion 64A in the finished filter 64), is preferably heat set to a more compressed configuration than the remaining portions of the tube 63.

Figure 30:
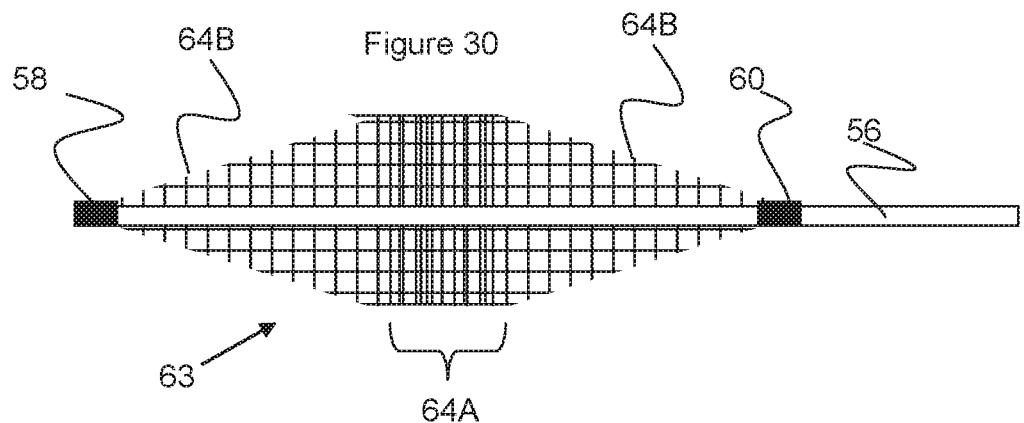

Referring to FIG. 30, a proximal end of the tube 63 is crimped on to tube 56 via fixed joint member 58 and a proximal end of the tube 63 is connected to sliding joint 60 to the tube 56. This arrangement creates a mesh structure with two conical ends 64B.

Figure 31:
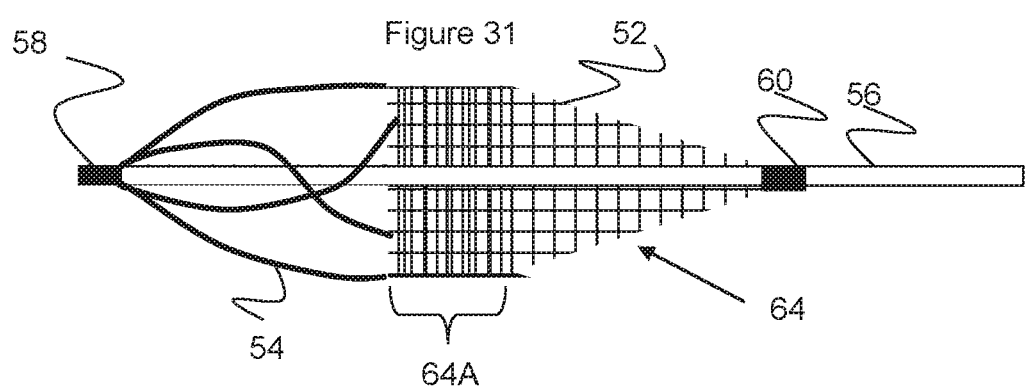

Referring to FIG. 31, only the smaller diameter wires 52 are then trimmed, such that only the larger diameter wires 54 remain on the proximal end of the device 50. In one example, the wires 52 are trimmed just proximal of the end portion 64A and against fixed joint 58. Preferably, as seen in FIG. 28, the free ends of wires 52 around the opening of the filter 64 are electro-polished to reduce any traumatic or abrasive tendencies. Finally, a second distal, flexible tube 62 (see FIG. 25) is fixed to the end of the tube 56 to provide the device 50 with an atraumatic tip. Flexible tube 62 may be polymeric (i.e. PTFE) or metallic, and can have a consistent or variable stiffness profile. A variable stiffness profile would be useful to have a graduated stiffness along the length of the tube, where the distal most portion (likely to contact the vessel) will be more flexible. This variable stiffness profile can be achieved by using various polymers or metals along the length of the tube with different material profiles. In one example, a laser cut spiral pattern is utilized on the metallic or polymeric tube. A coil may be positioned under the tube, with the polymer heat set over the coil (i.e. heat shrunk tubing). This coil would provide additional flexibility to the flexible tube section. Flexible tube 62 contains a channel which the guidewire sits through to enable tracking through the vasculature.

Optionally, as seen in FIG. 27, one or more radiopaque markers 53 can be fixed at various locations on the filter 64. For example, markers 53 can be fixed to the larger wires 54 at locations near the end portion 64A or at the free edge of the filter 64 (i.e., near the electro-polished free ends of the wires 52).

Figure 32:
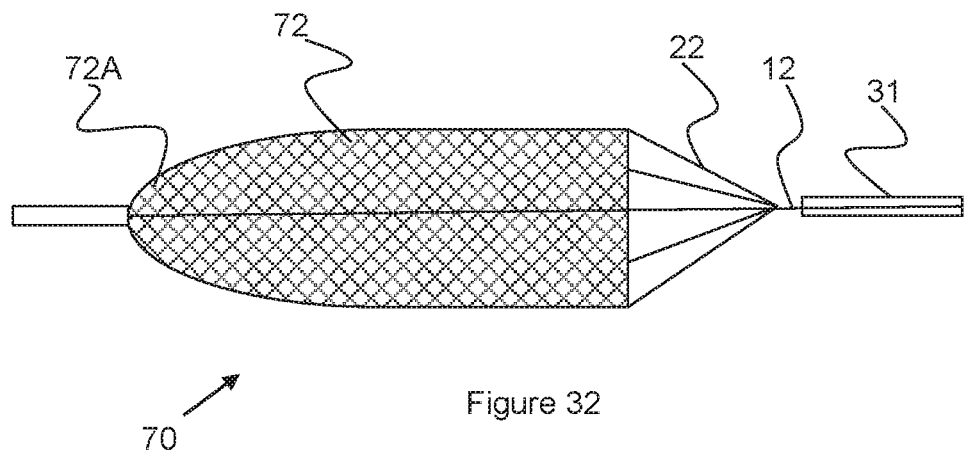
FIG. 32 illustrates an embolic protection device having a parabolic filter shape.

FIG. 32 illustrates yet another embodiment of an embolic protection device 70 that is generally similar to the previously described embodiments, but further includes a generally parabolic shape of its filter 72. By providing a more rounded distal end 72A to the filter 72 instead of a more straight or linear decrease, the pore size of the filter's mesh can remain more consistent and therefore improve distal blood flow through it.

Figure 33:
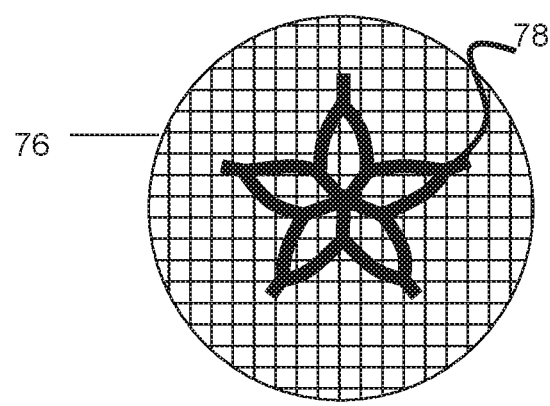
FIG. 33 illustrates an end view of a filter having a plurality of loop-shaped struts.

FIG. 33, illustrates a distal end view of a filter 76 having a plurality of struts or larger diameter wires that form a support basket 78 for the mesh of the filter 76. Generally, the basket 78 provides additional support and even assists in expansion/contraction of the filter 76. In one embodiment, the wire of the basket 78 is composed of Nitinol and is heat set to a desired "open" or expanded configuration. The basket 78 can be located within the filter 76, woven within the filter's mesh, or located on and fixed to an outer side of the filter 76.

Figure 34:
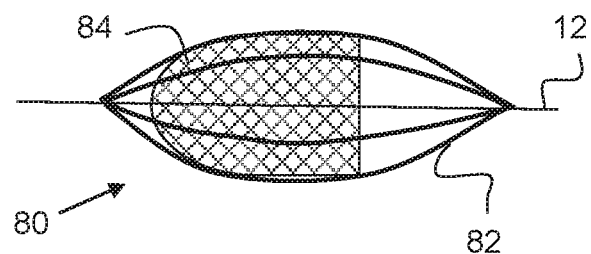
FIGS. 34-35 illustrate an embolic protection device having outer, "football" shaped struts.
Figure 35:
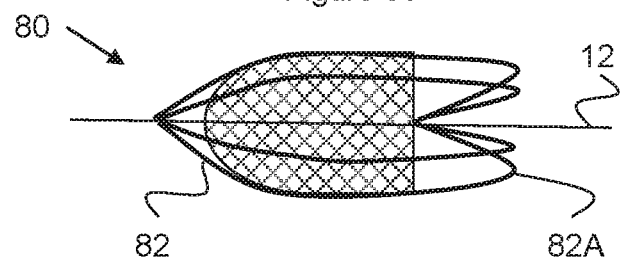

FIGS. 34 and 35 illustrate another embodiment of an embolic protection device 80, having a plurality of elongated struts 82 that are fixed to a filter 84. The struts 82 can be heat-set to a configuration of either the football/elliptical shape of FIG. 34 or the partially inverted shape of FIG. 35, and can both be compressed and deployed in those shapes. Alternately, the struts 82 can be heat-set to have the expanded, partially-inverted shape of FIG. 35, but can be loaded into a delivery device 30 in the shape of FIG. 34, thereby self-inverting to the shape of FIG. 35 after deployment. In any of these embodiments, the struts can be formed by laser-cutting a Nitinol tube to create a "unibody" framework to help evenly distribute force along a vessel's wall.

Figure 36:
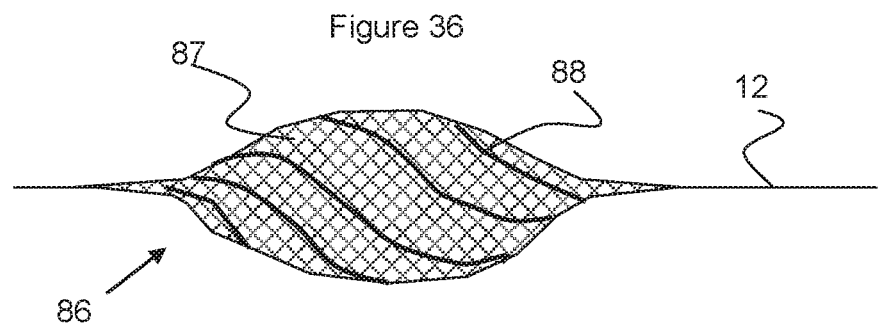
FIG. 36 illustrates an embolic protection device.

FIG. 36 illustrates another embodiment of an embolic protection device 86 having a generally oval or elliptical shape. This device 86 can be created with a tubular, stent-like structure, having larger diameter wires 88 and smaller diameter wires 87 woven together. As with other embodiments described in this specification, the proximal end can be crimped or connected via a fixed joint to a delivery wire 12, while the distal end can be connected via sliding joint to the delivery wire 12.

As previously discussed with regard to the device 50 of FIG. 25, for example, the proximal-most portion of the devices of this specification, such as the fixed joint 58, can accommodate both a delivery wire 12 (which the device is disposed on) as well as a guidewire 40, which thereby acts as a monorail or rapid exchange catheter. It should be understood that several different configurations are possible to accommodate these wires 12, 40, examples of which are illustrated in FIGS. 37-44.

Figure 37:
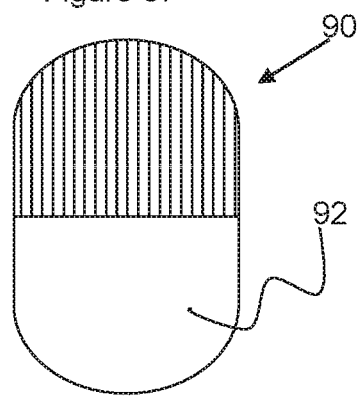
FIGS. 37-40 illustrate cross sectional views of various rapid exchange embolic protection devices.
Figure 38:
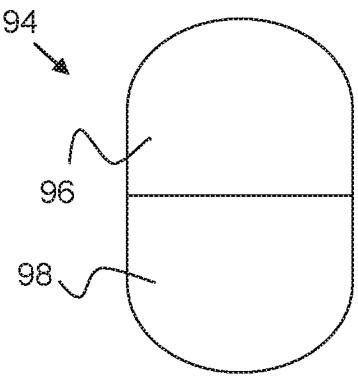

FIGS. 37-38 illustrate other configurations of rapid exchange catheter ports involving variations of FIGS. 17-18. The port would comprise one large opening segmented into two parts, the more distal port (i.e. 96) would be used for the guidewire while the more proximal port (i.e. 98) would be used for the embolic protection device. As shown in FIG. 37 one of the ports could be perforated (i.e. more distal port 90) to provide some tactile reference of which port is used for which purpose.

Figure 39:
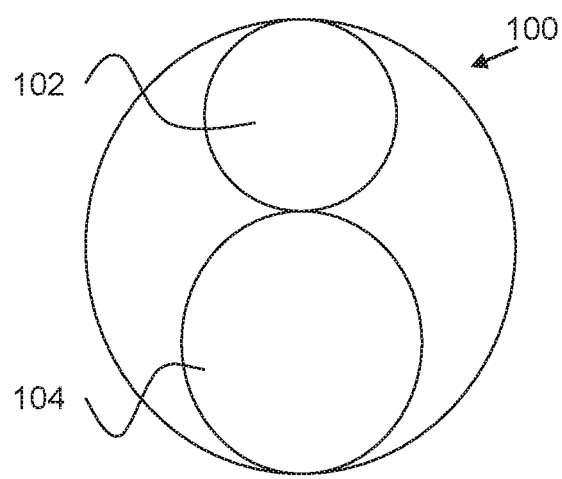
Figure 40:
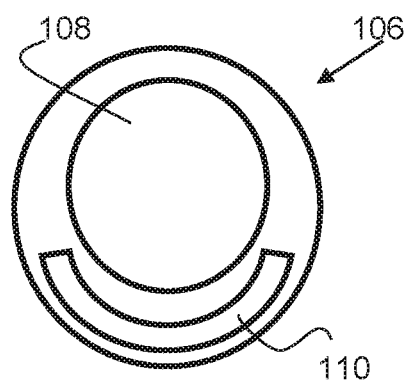

FIGS. 39-40 illustrate various example cross-sectional configurations of a fixed joint or proximal-most portion of device embodiments with a rapid exchange capability. In FIG. 39, cross section 100 includes a first passage 102 and a second passage 104, where one of the passages may accommodate guidewire 40 and the other accommodates delivery wire 12. FIG. 40 illustrates a cross section 106 having a first, round passage 108 for guidewire 40 and a second arc-shaped passage 110 for the delivery wire 12. In this example, the delivery wire 12 would also be generally arc-shaped so as to fit within the passage 110. The passage 110 is also preferably located relatively close to the passage 108 and has an inner arc shape that is somewhat larger than the diameter of the passage 108, reducing the overall diameter of the device.

Figure 41:
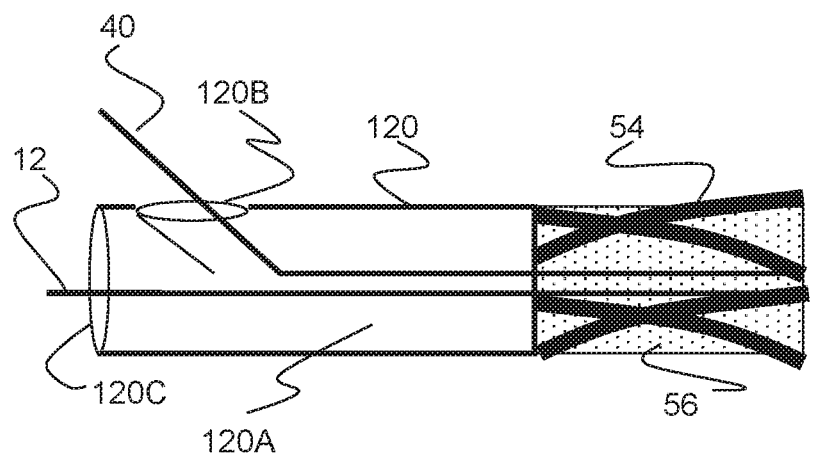
FIGS. 41-44 illustrates side views of various rapid exchange embolic protection devices.

Turning to FIGS. 41-44, these embodiments disclose various example port and passage locations. Turning to FIG. 41, a fixed joint 120 is illustrated, having a first port 120C and a second port 120B that both lead to the same internal passage 120A. Hence, the delivery wire 12 can pass directly through port 120C, while the guidewire can pass, somewhat skewed of center via port 40, while sharing the same passage 120A through the device.

Figure 42:
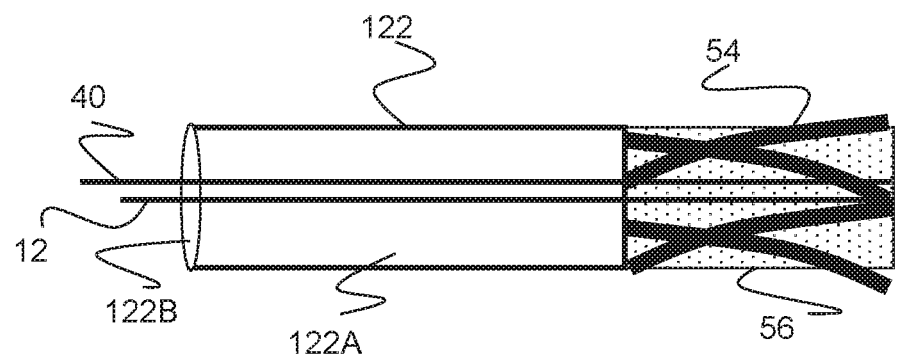

In FIG. 42, the fixed joint 122 includes only a single port 122B and single passage 122A through the device. Hence, delivery wire 12 and guidewire 40 can share both the port 122B and the passage 122A.

Figure 43:
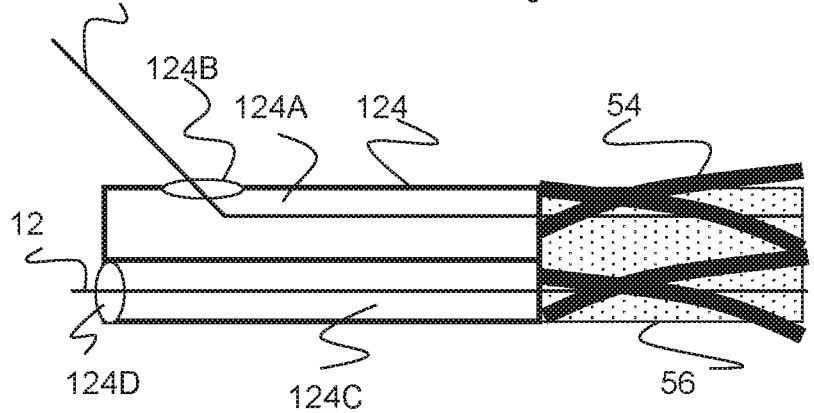

Turning now to FIG. 43, the joint 124 includes a first passage 124A opening to port 124B, and a second passage 124C opening to port 124D. In this respect, the guidewire 40 can travel through its own passage 124A and port 124B, while the delivery wire 12 can operate in passage 124C and passage 124D.

Figure 44:
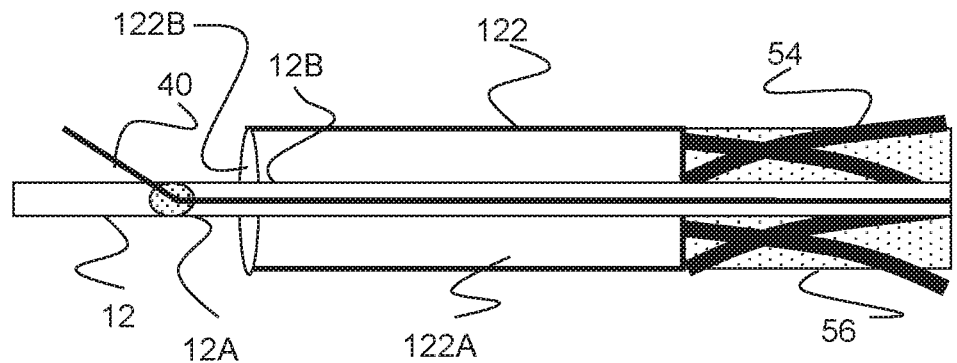

Finally, FIG. 44 illustrates a joint 122 with a single passage 122A and port 122B, similar to that shown in FIG. 42. However, the delivery wire 12 further comprises its own internal guidewire passage 12b that opens proximally at port 12B and near a distal end of the device. The port 12A is preferably located such that it is proximal of the joint 122 during normal operation. In this respect, the guidewire 40 can pass into the device (e.g., through an atraumatic end) and into a distal end of the wire 12, into its passage 12B and finally out its port 12A. Preferably, the passage 12B and port 12A are sized so as to accommodate a guidewire 40. Alternatively, the joint itself may include a port such as port 124B of FIG. 43, and this port leads into a port within the delivery wire which the guidewire can be inserted through.

Proximal joint 58 and distal joint 60 may have different configurations as well aside from the fixed proximal, translatable distal examples discussed earlier. For example, proximal joint 58 may have some translational capability (via one or more stops placed in proximity to said proximal joint) and/or some rotational capability via the joint not being complete fixed to tube 56. Distal joint 60 may have more limited translational capability via the inclusion of one or more stops placed in the proximity of the joint, and/or some rotational capability via the joint not being completely fixed to tube 56.

Figure 45:
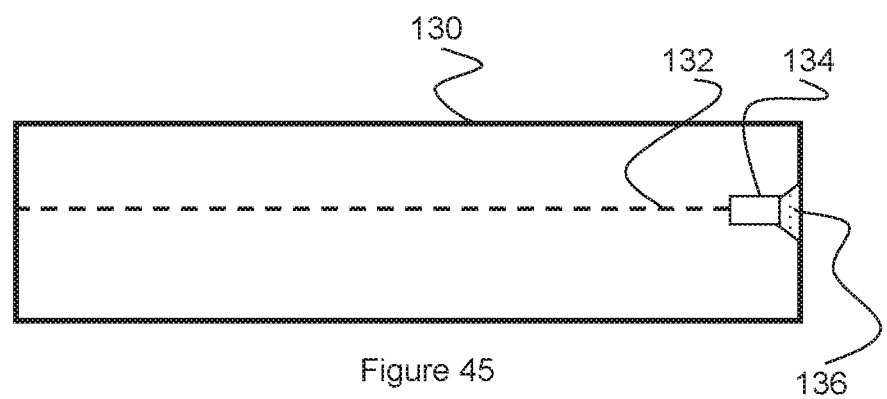
Figure 46:
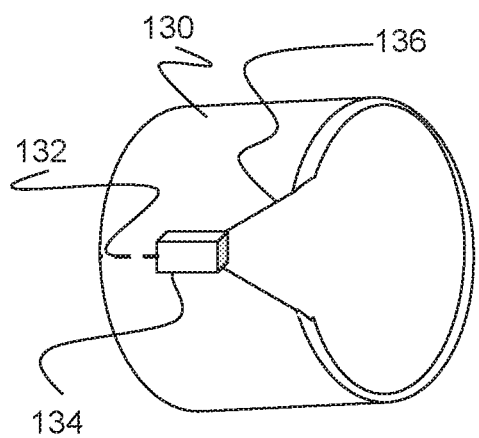
FIG. 46 illustrates a catheter-cutting device for opening a distal end of a delivery device.

Another aspect of a delivery device, such as a microcatheter, allows the distal end of the delivery device to open or expand, thereby creating a somewhat tapered distal end to facilitate gentle deployment and retraction of the various embolic protection devices of this specification. In one example shown in FIGS. 45 and 46, a cut or slit 136 in a delivery device 130 can be created just prior to deployment of an embolic protection device. An opening device 134, shaped to cut or rip the wall of the delivery device 130, can be located at or near the very distal end of the device 130. a wire 132 is connected to the opening device 134 and extends to a proximal end of the device 130, allowing the physician to pull the opening device 134, creating a cut. In one embodiment, the wire 132 is located within its own passage within the delivery device 130. In another embodiment, a perforation is located along the wall of the delivery device 130 to assist in the creation of the cut. In another embodiment, the distal end of the delivery device 130 includes a "C" shaped metal component that is biased to outwardly expand subsequent to creation of the cut 136.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An embolic protection device, comprising:
an elongated body member; and,
a mesh filter having an expanded conical shape defined by an open proximal face opening to an interior of said expanded conical shape, and by a proximal edge region located around said open proximal face to said interior of said expanded conical shape; said mesh filter comprising a first plurality of woven wires and said expanded conical shape having a first radial size;
wherein said proximal edge region can be selectively proximally expanded in length and decreased in diameter relative to a remaining portion of said mesh filter while substantially maintaining said first radial size of said expanded conical shape, to at least partially close around particles captured in said mesh filter;
wherein said proximal edge region is less porous than a remaining distal region of said conical shape.

2. The embolic protection device of claim 1, further comprising a second plurality of wires that are partially woven with said first plurality of woven wires, and that further extend proximally from said proximal edge region of said conical shape and having proximal ends coupled to said elongated body.

3. The embolic protection device of claim 2, further comprising a fixed joint connected to said elongated body member and to said proximal ends of said second plurality of wires.

4. The embolic protection device of claim 3, further comprising a sliding joint connected to said elongated body member to slide relative thereto, and further connected to said first plurality of wires.

5. The embolic protection device of claim 2, wherein said first plurality of wires have a diameter within a range of about 0.0005-0.00225 inch and wherein said second plurality of wires have a diameter of about 0.00225-0.008 inch.

6. The embolic protection device of claim 2, wherein said first plurality of woven wires are in a range of 72 to 288 wires, and said second plurality of wires are in a range of 4 to 16 wires.

7. The embolic protection device of claim 1, wherein said proximal edge region is heat set to form a more compressed configuration when said mesh filter is expanded to said expanded conical shape of said first radial size, as compared with said remaining distal region of said conical shape.

8. The embolic protection device of claim 1, wherein said proximal edge region has a different weave pattern than said remaining distal region of said conical shape.

9. An embolic protection device, comprising:
an elongated body member; and,
a mesh filter comprising a plurality of woven wires;
wherein said mesh filter has a compressed first configuration being radially sized to fit within a delivery catheter;
wherein said mesh filter has a second configuration being fully radially expanded; wherein said plurality of woven wires form a conical shape defined by a proximal opening into an interior of said conical shape, and defined by a proximal edge portion located radially around said proximal opening; said proximal edge portion having a first diameter and having a different weave pattern than said remaining portion of said mesh filter; and,
wherein said different weave pattern causes said proximal edge portion of said mesh filter to move to a third configuration in which said proximal edge portion of said plurality of woven wires have a second diameter that is smaller than said first diameter while substantially maintaining a radial size of said conical shape from said second configuration, so as to at least partially close said proximal opening around particles captured in said interior of said mesh filter.

10. The embolic protection device of claim 9, further comprising a plurality of struts woven with said plurality of woven wires and extending proximally from said mesh filter.

11. The embolic protection device of claim 10, wherein said struts have a larger diameter than said plurality of woven wires.

12. The embolic protection device of claim 9, wherein said proximal edge portion of said mesh filter is less porous than a remaining distal portion of said mesh filter.

13. The embolic protection device of claim 12, wherein said proximal edge portion is heat set to form a more compressed configuration when said mesh filter is fully, radially expanded in said second configuration, as compared with said remaining distal portion of said mesh filter.

14. An embolic protection device, comprising:
an elongated body member; and,
a mesh filter having an expanded conical shape defined by an open proximal face opening to an interior of said expanded conical shape, and by a proximal edge region located around said open proximal face to said interior of said expanded conical shape; said mesh filter comprising a first plurality of woven wires and said expanded conical shape having a first radial size;
wherein said proximal edge region is heat set to move from a longitudinally compressed configuration relative to a remaining portion of said mesh filter in said first radial size to a longitudinally expanded configuration that is decreased in diameter while substantially maintaining said first radial size of said expanded conical shape, to at least partially close around particles captured in said mesh filter;
wherein said proximal edge region is less porous than a remaining distal region of said conical shape.

* * * * *